United States Patent [19]

Mercaldi

[11] Patent Number: 4,856,233

[45] Date of Patent: Aug. 15, 1989

[54] METHOD FOR SAMPLING A WORKPIECE

[75] Inventor: David W. Mercaldi, Sudbury, Mass.

[73] Assignee: Failure Analysis Associates, Inc., Palo Alto, Calif.

[21] Appl. No.: 258,471

[22] Filed: Oct. 17, 1988

Related U.S. Application Data

[62] Division of Ser. No. 17,632, Feb. 24, 1987.

[51] Int. Cl.⁴ .................. B24B 19/00; G01N 1/04
[52] U.S. Cl. .................. 51/281 R; 51/33 R;
    51/99; 51/126; 73/864.41
[58] Field of Search .......... 51/33 R, 58, 59, 99,
    51/126, 206 R, 209 R, 281 R, 290; 73/864.41,
    864.81; 81/490, 491; 83/54, 490, 491, 861, 919;
    125/13 SS; 408/150; 409/143

[56] References Cited

U.S. PATENT DOCUMENTS

| | | | |
|---|---|---|---|
| 122,514 | 1/1872 | Bullock | 51/206 R |
| 3,159,952 | 12/1964 | Lipkins | 51/206 R |
| 3,374,586 | 3/1968 | Stone | 51/206 R |
| 3,780,435 | 12/1973 | Farha et al. | 83/178 |
| 3,857,425 | 12/1974 | Wikland | 83/491 X |
| 4,252,152 | 2/1981 | Martin et al. | 138/97 |
| 4,304,139 | 12/1981 | Johnson | 73/864.41 X |
| 4,372,174 | 2/1983 | Cymbalisty et al. | 73/864.41 X |
| 4,598,597 | 7/1986 | Widner et al. | 73/864.41 X |

OTHER PUBLICATIONS

Grimsley's House of Tools Inc., Portsmouth, Va., Grimsley's Portable Trepanning Metal Cutting Machine, Model WP-1, Jun. 1, 1987.

*Primary Examiner*—Robert P. Olszewski
*Attorney, Agent, or Firm*—Shlesinger & Myers

[57] ABSTRACT

A method for sampling a workpiece and for retaining the sample in the workpiece so that it may be retrieved by using a semi-spherical cutting blade rotated about its central axis and articulated about an axis perpendicular thereto such that the cutting action follows a single arcuate path enabling a cut to be made in a workpiece which is relatively shallow and smooth, thereby providing under normal circumstances a non-destructive, partial-spherical recess in the workpiece sampled which does not have to be repaired before placing the workpiece back into service, while at the same time forming a sample of significant depth and size adequate for accurate analysis.

17 Claims, 5 Drawing Sheets

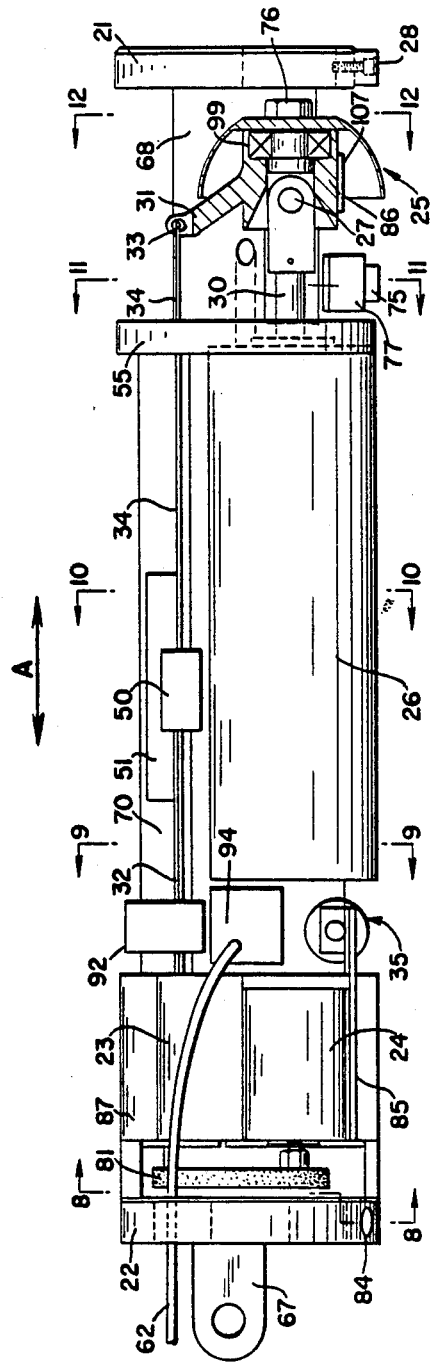

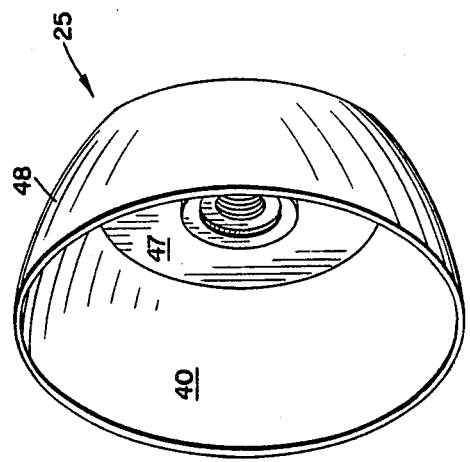
Fig. 3
Fig. 4
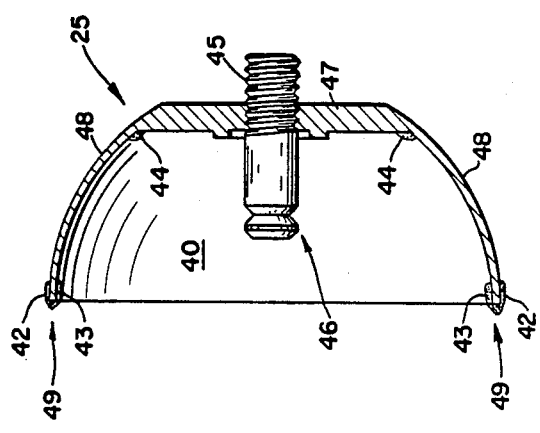
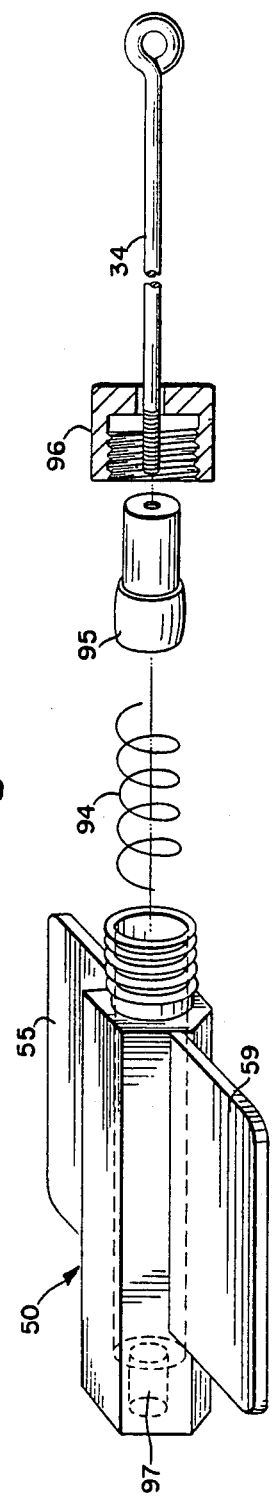
Fig. 5

METHOD FOR SAMPLING A WORKPIECE

This is a division of application Ser. No 017,632 filed Feb. 24, 1987.

BACKGROUND OF THE INVENTION

The present invention relates to devices for obtaining and retrieving a sample of material for analysis. More particularly, the present invention relates to sampling devices which detach and retrieve a portion of the surface of a material for analysis of surface features and of the underlying material, such as, for example, of the inner portions of pipes found in electric generating "power" plants.

It is often necessary to test or examine material which has been subjected to a somewhat hostile operating environment. In order to accurately, quantitatively, determine the properties of a material, a sample must be obtained from the material for testing. Further, any detailed metallurgical examination requires a sample of material for laboratory analysis. The need for testing or examination of structural materials in remote locations can arise in a number of situations, including the interior of a pipe or conduit which transports material at temperatures and pressures which can cause changes in the mechanical properties of the material composing the pipe over its service life. Also, other equipment which is subjected to stress, and thermal, radiation, chemical, or other environmental conditions may need to be sampled and tested to determine the damaging effects caused by such conditions.

The effects of exposure to hostile environments, and mechanical and thermal stress can produce severe problems in many situations and with many types of equipment. Notably, an acute problem has developed in aging power plants which have been in service for long periods of time. The turbines which are utilized to generate power from steam are subjected to thermal, mechanical and corrosive stresses. These stresses can cause failure of all or part of a turbine. If no data is available as to the condition of the materials which compose the components of the turbine then an uninformed decision has to be made as to whether to continue to run the turbines without knowing their true condition; thus presenting the undesirable dilemma of either incurring a significant risk of failure or replacing, prematurely, the turbines prior to the expiration of their useful life. Continuing to run a turbine which has unknowingly become unreliable can, of course, result in catastrophic failure. In addition to the potential tragedy of human injury, there is the enormous expense, in such a situation of having to replace the entire turbine, simply because one component failed.

For the above reasons, at least, there is a great need for a means for determining the condition of the material components of turbines and similar mechanical structures which undergo stress over a prolonged period of time. There is in this respect, a great need to be able to predict the remaining useful life of these machines and their material components. Unfortunately, prior to the advent of the present invention, it was often not possible to accurately measure the present condition of materials subjected to long term stress without destroying or significantly deforming the material components of the mechanism to be tested or completely dissembling the mechanism to be inspected. Under certain prior art sampling techniques, for example, great expense and time was necessary to repair the damage done through the sampling process.

Many techniques have been developed in the prior art for obtaining a sample for analysis, in an attempt to mitigate the above problems. None has been truly successful in permitting sample removal from remote locations with minimal structural consequences. One technique, for example, makes two cuts into a surface to form a V-shaped groove in the piece of material to be tested. The cuts are made along the entire length of the material in order for the triangular shaped section of material to be removed from the main portion of the material. If the cuts are not along the entire length, two further cuts are needed at either end in order to release the triangular sample, or, the two cuts may be made by a slightly cupped grinding wheel, yielding a sample shape which is typically described as a "boat sample". These processes require a large sample to be taken from the underlying material, and each leaves a sharp hole which needs later repair. This repair of the underlying material is often time consuming and expensive and will generally result in a weakened structure. Further, performing such an operation remotely is not practical.

Another prior art technique which permits obtaining some information about the material while causing little or no damage to the component is referred to as "replication". In this technique, the surface of the material is replicated by application of a coating, generally after some mechanical polishing and chemical etching of the surface has been performed. The coating is applied in liquid form and allowed to harden and is then peeled off to reveal a mirror image of the surface features of the underlying material. This technique only allows for examination of surface features and does not allow for analysis of the underlying material. Also, it is typically not possible to perform this technique in remote locations. The lack of an actual, physical sample of the underlying material is obviously a significant drawback when attempting to evaluate the condition of certain power plant/turbine components.

As alluded to above, it is also possible to analyze underlying material structures by partial or complete dismantling of the mechanism involved. It may then be possible to examine or sample material components of the mechanism by conventional techniques, followed by replacement of the worn out or damaged parts and reassembly. This often necessitates lengthy shut down periods and requires a large amount of time and expense in the disassembly and reassembly of complicated machinery.

In view of the above, it is apparent that there exists a need in the art for a sampling device which at least overcomes the above-described problems.

SUMMARY OF THE INVENTION

The subject invention, by a unique combination of elements, solves the above-described needs in the art and other needs, apparent to the skilled artisan once given the following disclosure:

It is an object of the present invention to provide a mechanism for obtaining a sample which can be analyzed for surface and/or sub-surface characteristics and to determine the physical parameters of the material from which the sample is taken.

It is a further object of the present invention to provide a device which can separate and retrieve a sample of material with minimal disruption to the underlying structure.

It is still a further object of the present invention to provide a device which can cut a sample from any surface of a solid piece of material.

It is yet another object of the present invention to provide a device which can cut a sample from a solid piece of material and retrieve the sample intact.

It is still another object of the present invention to provide a device which can remove a sample from a solid piece of material without disruption of the original surface of the sample, or of the base material contained in the sample.

These and other objectives are accomplished by the present invention which is comprised of a device for obtaining a sample of a substrate and surface comprising cutting means for separating said sample from said substrate, said cutting means including a generally hemispherically-shaped blade having an axis of rotation generally concentric with the center of said blade, first drive means connected to said blade for rotating said cutter about said axis, second drive means connected to said blade for articulating said cutting means whereby said blade is capable of separating said sample from said substrate by following an arcuate path, and means for retrieving said sample when separated from said substrate.

The present invention creates minimal disruption of the structure from which the sample is taken. A small semi-spherical depression is left in the underlying material in the location from which the sample was removed. The cutter of the present invention allows for a single pass in order to separate the sample from the remainder of the material. The single cut, made from one direction is smooth and continuous and therefore leaves no sharp edges.

The teachings of the present invention illustrate that sharp edges or discontinuities need to be avoided to minimize stress concentration around the sample taken. The depression formed in the underlying material is spherical and shallow thereby presenting the minimal distortion profile attainable.

In certain preferred embodiments, the depth of the cut can be controlled by the relative positioning of the carrier and the structure from which the sample is taken. A very accurate sample can therefore be obtained which maintains the sample surface intact for analysis. The blade in such an embodiment may be designed for minimum abrasive grinding by generation of a thin kerf for passage of the hemispherical blade.

The hemispherical cutter contemplated in certain further embodiments of the present invention may be of a mechanical cutting type, electrical discharge machining type or any other type cutter which can be configured to form a hemispherical cut line creating a minimal thickness kerf for travel of the blade.

A further advantage of the single pass cut of the present invention is that samples can be taken near junctures of differing planes within the mechanism. A cut near such a corner can be made because all drive and support means can be located on one side of the cutter, permitting placement of the cutter itself deep into the corner from one side as opposed to some previously described sampling methods requiring two cuts from opposing directions.

This invention will now by described with respect to certain embodiments as illustrated in the following drawings:

BRIEF DESCRIPTION OF THE DRAWINGS

FIG. 1 is a side view of a preferred embodiment of the present invention.

FIG. 2 is a top view of a preferred embodiment of the present invention.

FIG. 3 is a cross-sectional side view of the hemispherical blade of a preferred embodiment of the present invention.

FIG. 4 is a perspective view of a preferred embodiment of the hemispherical cutting blade of the present invention.

FIG. 5 is an assembly view of the rotational-to-linear motion translation assembly.

DETAILED DESCRIPTION OF A PREFERRED EXEMPLARY EMBODIMENT

Figure 6:
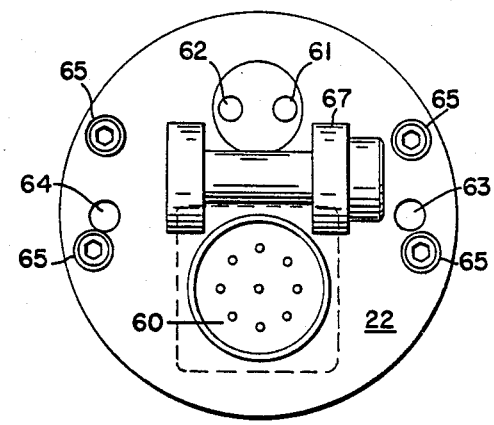
FIG. 6 is a back end view of a preferred embodiment of the present invention.
Figure 7:
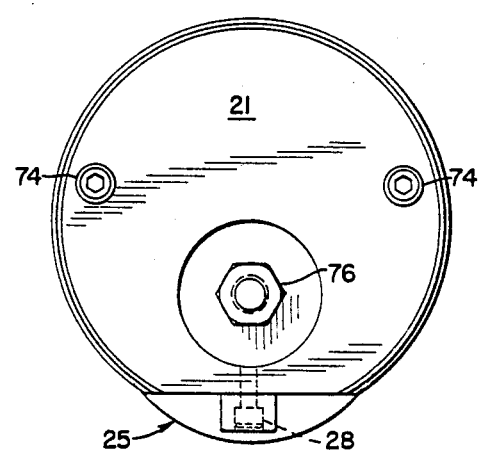
FIG. 7 is a front end view of a preferred embodiment of the present invention.

FIGS. 1 and 2 illustrate an embodiment of the present invention, wherein a wheeled carriage is utilized to transport the cutting blade and its associated drive mechanisms to the desired sampling site. As illustrated hemispherical cutter 25 is located towards the forward end of the carriage. The opposite end of the carriage is defined by backend bulkhead 22, upon which is mounted bracket 67 for attachment of positioning handle 98 which is utilized to position the carriage by rolling on wheels 35 and 36. The front end of the carriage is supported by spring-biased front skid 75 (illustrated more completely in FIG. 11) which is biased by spring 78 to extend beyond the cutter 25 to protect the blade 48 from contacting the surface when the carriage is not secured in position. Front skid 75 is protected against over-extension by spring retainer 77, mounted to backplate 79.

Figure 8:
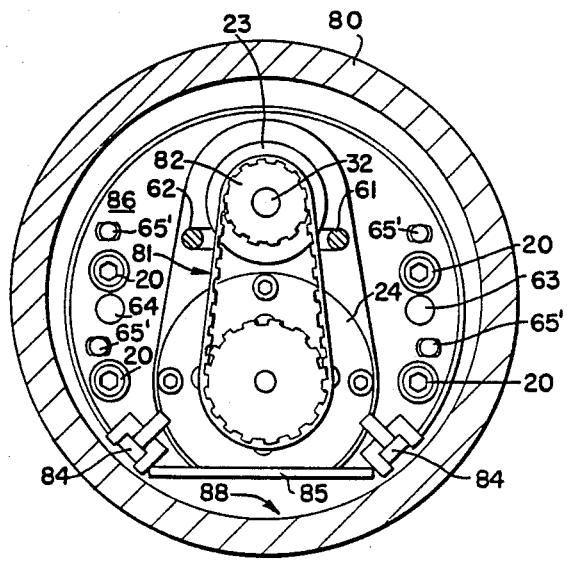
FIG. 8 is a cross sectional view taken along line 8—8 of FIGS. 1 and 2.

The backend bulkhead 22, as illustrated in FIG. 6, is bolted to the stepper motor housing 86 by bolts 65 which thread into holes 65′ (as better illustrated in FIG. 8). Backend bulkhead 22 also has electrical connector 60 mounted thereon for receiving the electrical connector which carries the appropriate control signals for stepper motor 24 and drive motor 26. Bulkhead 22 has further openings for provision of coolant and vacuum lines 63 and 64 which extend the length of the carriage to provide coolant to the cutter 25 and the sampling area, and remove spent coolant from the region. Coolant access paths 63 and 64 extend throughout the length of the carriage, as can be seen in FIGS. 2 and 8-12.

Figure 10:
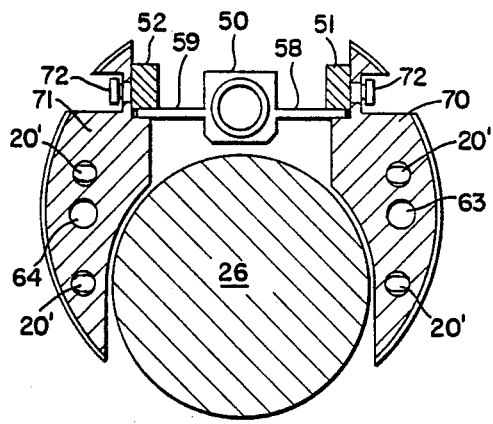
FIG. 10 is a cross sectional view taken along line 10—10 of FIGS. 1 and 2.

Stepper motor housing 87 is in turn bolted to the two drive motor housing members 70 and 71, illustrated in FIG. 10. Bolts 20 are utilized to secure the stepper motor housing 87 to the threaded holes 20' of the drive motor housing halves 70 and 71. As further illustrated in FIG. 8, stepper motor 24 is associated with toothed gear 83 and drive screw support bearing housing 23 is associated with drive screw toothed gear 82. Stepper belt 81 is utilized to link gears 82 and 83. The drive screw 32 is directly coupled to gear 82. As can be seen, Gear 83 is turned in controlled steps by controlled activation of stepper motor 24. Drive screw 32 is therefore rotated in precise discrete amounts through controlled actuation of stepper motor 24.

Figure 14:
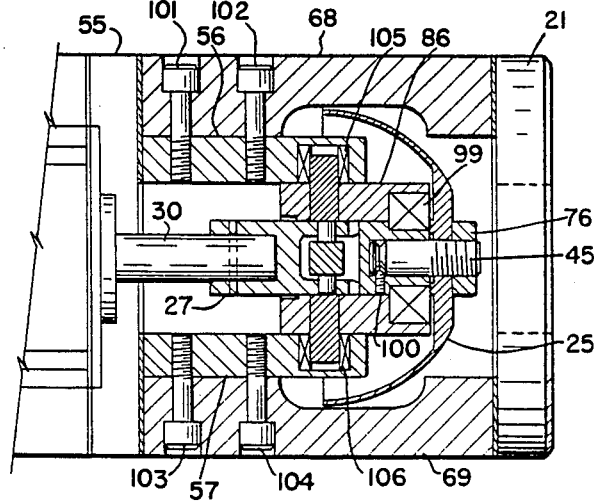
FIG. 14 is a top view of a horizontal cross-section of the cutting head taken at the cutter centerline.

Rotation of drive screw 32 is utilized to pivot cutter 25 into and out of engagement with the surface to be sampled. Drive screw 32 extends from gear 82 and into drive member 50. FIG. 5 illustrates the mechanism within drive member 50 for translation of the rotation of drive screw 32 into horizontal motion on push rod 34 to actuate the tilting of cutter 25 by pushing and pulling of arm 31 of the cutter trunnion 86 at pivot point 33. Push rod 34 will flex to accommodate the vertical motion of pivot point 33 that occurs due to its path of rotation. Trunnion 86 exerts force on the cutter shaft 45 through ring bearing 99 disposed between trunnion 86 and the cutter side of universal joint 27, in which shaft 45 is inserted and retained by set screw 100 (FIG. 14). The force of trunnion 86 therefore acts to tilt cutter 25 about the axis of trunnion bearings 105 and 106, which axis also passes through the center of action of universal joint 27, and the center of curvature of cutter 25.

The threaded end of drive screw 32 (illustrated in FIG. 1) is mated into the threaded hole 97 in one end of drive member 50. As drive screw 32 is rotated., drive member 50 will travel linearly along the longitudinal axis of drive screw 32. Drive member 50 is prevented from rotation by the engagement of wings 58 and 59 into the slots created between block 51 and drive motor housing member 70 and the block 52 and drive motor housing member 71 illustrated in FIG. 10. The wings 58 and 59 of drive member 50 slide along these slots to allow linear motion of drive member 50 while preventing its rotation.

Plunger 95 is threaded securely to the end of push rod 34, which extends through end cap 96. Plunger 95 is then inserted against biasing spring 94 inside the hollow portion of drive member 50. End cap 96 is then secured to the open end of drive member 50. This arrangement allows for compliance in the transmission of force from block 50 to push rod 34, to assure smooth advance of cutter 25 despite the incremental motion of block 50, as driven by stepper motor 24. Spring 94 allows some relative movement of plunger 95 within block 50. This compliance also acts to limit the force applied to pivot cutter 25. Blocks 51 and 52 are held in position by bolts 72.

Figure 9:
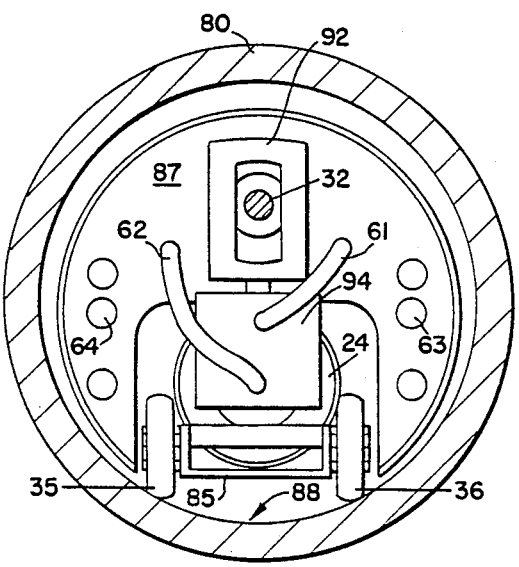
FIG. 9 is a cross sectional view taken along line 9—9 of FIGS. 1 and 2.

Wheels 35 and 36 as illustrated in FIG. 9, are mounted to an axle attached to spring plate 85. Plate 85 is attached at its opposite end to the stepper motor housing 86, thereby allowing the end to which the wheels 35 and 36 are attached to move upwardly and downwardly freely. Spring member 85 is biased so that wheels 35 and 36 will normally extend downwardly to extend beyond the outer circumference of the carriage, thereby contacting the surface upon which the carriage is riding.

Figure 11:
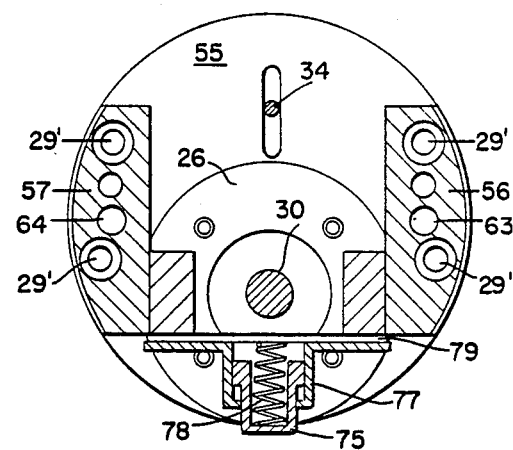
FIG. 11 is a cross sectional view taken along line 11—11 of FIGS. 1 and 2.
Figure 12:
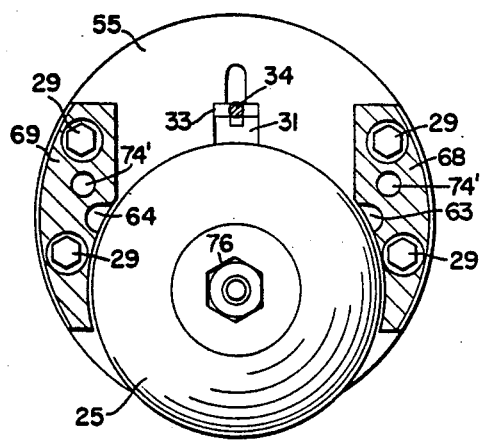
FIG. 12 is a cross sectional view taken along line 12—12 of FIGS. 1 and 2 of the present invention.

FIG. 11 illustrates the drive motor mounting bulkhead 55 to which the drive motor 26 is secured. Motor mount bulkhead 55 has an elongated slot through which pushrod 34 extends. Pushrod 34 then attaches to arm 31 at pivot 33, as illustrated in FIG. 12. Also in FIG. 12 the cutter 25 is shown secured to shaft 45 by nut 76. The cutter shaft 45 is linked to the drive motor shaft 30 through universal joint 27, thus allowing free pivoting of the cutter. Cutter support members 68 and 69 are bolted to the motor mount bulkhead 55 by bolts 29. illustrated in FIG. 12, which extend through holes 29' illustrated in FIG. 11, and are secured into threaded holes in the motor mount bulkhead 55. Similarly the front end bulkhead 21 is secured to the blade support members 68 and 69 by bolts 74, engaged in threaded holes 74'.

FIG. 14 illustrates that trunnion bearings 105 and 106 are housed by trunnion support members 56 and 57. Members 56 and 57 are attached to cutter support members 68 and 69 by capscrews 101 through 104.

The air cylinder 94 and pressure foot 92, utilized to lock the carriage in position for sampling, are illustrated in FIG. 9. Through proper control of air supply and return lines 61 and 62, air cylinder 94 is actuated to extend pressure foot 92 to engage the interior surface of a tube such as 80. Pressure foot 92 is slotted to permit passage of drive shaft 32.

Figure 13A:
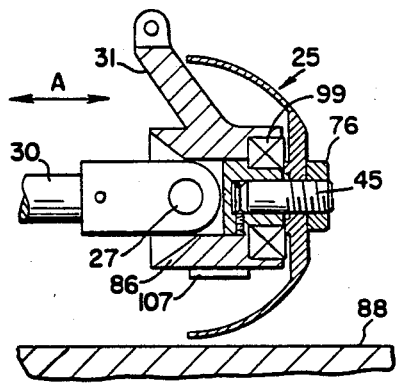
FIGS. 13A-E are simplified, partially schematized, views illustrating the present invention in use taking a sample from a surface.

The entire carriage is first positioned along the length of the tube by use of a rod 98 to push or pull the carriage in the directions indicated by arrow A (FIGS. 1,2 and 13A) to the desired location. The carriage rolls along wheels 35 and 36, and slides along front skid 75, which prevents contact of the cutter 25 with the interior surface of the pipe 80. Once the carriage has been located in the desired position, pressure foot 92 is extended through actuation of air cylinder 94 and is forced into engagement with the upper interior surface of pipe 80. As pressure foot 92 continues to exert force, both front skid 75 and wheels 35 and 36 are forced to retract against their spring-biased mechanisms. The entire carriage will approach surface 88 until support pads 28, 83 and 84 contact the lower surface 88 of the interior of pipe 80. Support pads 28,83 and 84 are adjusted prior to positioning of the mechanism, so that when the carriage is forced down against the pads, the carriage will rest a predetermined, desired distance off of the surface 88 to be sampled, which will determine the thickness of the sample to be removed.

Figure 13B:
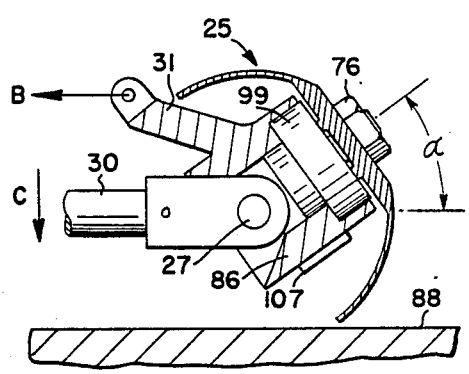
Figure 13C:
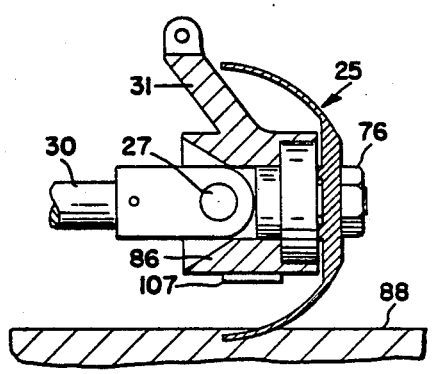
Figure 13D:
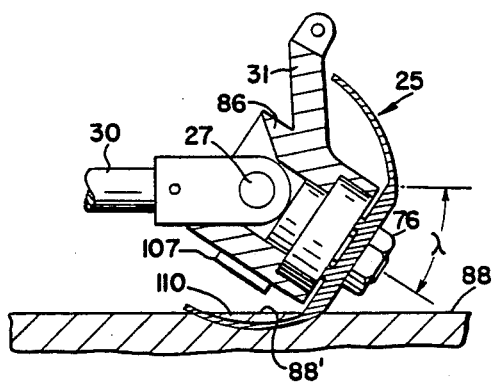
Figure 13E:
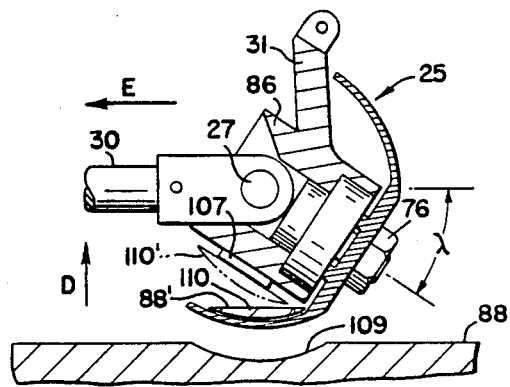

Once the carriage has been locked in position through force exerted by pressure foot 92 to cause the carriage to rest firmly on support pads 28, 83 and 84, the cutting process illustrated in FIGS. 13A-D may commence. Arrow A, (FIG. 13A) illustrates the horizontal positioning of cutter 25. Prior to being locked in position as described above, cutter 25 was retracted as illustrated in FIG. 13B in the direction of Arrow B. The entire carriage carrying cutter 25 is then forced in the direction of Arrow C against support pads 28, 83 and 84 by the clamping mechanism described above. After the positioning and clamping of the assembly, cutter 25 is then rotated in a direction opposite that of Arrow B from its retracted position. This is illustrated in FIG. 13C, i.e. a partial cut, and then sequentially in FIG. 13D, which is the final cut and separation of the sample to be collected and analyzed. This is accomplished, as aforesaid, through actuation of stepper motor 24 which rotates drive screw 32 to push pushrod 34, thereby tilting trunnion 86 through arm 31. Once the cut is complete, spinning of the cutter 25 is ceased by deactuation of drive motor 26. Cutter 25 remains in its fully-extended position, (FIG. 13D), in order to retain the extracted sample 110. For certain materials, a magnet 107 attached to the underside of trunnion 86 may be used to capture the sample, as indicated by position 110' in FIG. 13E. The pressure on pad 92 is relieved by deactuation of air cylinder 94. The carriage then raises up in the direction of Arrow D, (FIG. 13E), to ride once again on wheels 35 and 36 and front slide member 75. Cutter 25 is now clear of the interior surface of tube 80 and the carriage may be retreived in the direction of Arrow E, while cutter 25 is in its fully-extended position (FIG. 13E). Sample 110 is supported within the bowl of cutter 25 for retrieval (as illustrated in FIG. 13E).

Once extracted, the surface 88' of sample 110 can be analyzed. Also the sample 110 can be analyzed or tested for characteristics of the substrate material, thusly providing a means for analyzing both surface and material characteristics, while leaving a minimally disruptive dimple 109 in the original surface 88.

Blade 25 (as illustrated in FIG. 13B) is retractable through angle o wherein the axis of rotation of the blade is preferably about 30 to 32 degrees above horizontal. Similarly, as illustrated in FIGS. 13D and 13E, blade 25 is preferably designed to travel through angle λ below horizontal to complete the cut which severs sample 110. Angle λ is preferably about 30 to 32 degrees.

A particularly preferred embodiment of cutter 25 is illustrated in FIGS. 3 and 4 and is of a hemispherical shape, with a central, threaded hole to accommodate cutter shaft 45. Cutter shaft 45 has a notched end 46 for engagement by set screw 100 within universal joint 27. The cutter has a thick body portion 47 and a thin curved blade portion 48, which combine to form an essentially bowl-like structure. A thin coating of abrasive grit, which enables the blade to cut, is applied at the outer tip of the blade periphery, along the exterior surface at 42, along the interior at 43 and along the leading edge 49 of the blade. The entire length of the blade 48 is not provided with grit for cutting, so as to provide clearance for the noncutting portion of the blade and to minimize the opportunity for extraneous scratching of the surface of the sample or substrate. The very interior corner where the blade 48 meets the body 47 also contains a thin ring of cutting grit 44. This ring of grit 44 is provided to enable the first edge of a larger sample to be worn away, if necessary, thereby enabling the blade to obtain a deeper sample without jamming of the initial sample edge against the body 47 of the cutter 25.

Cutter 25 need not be precisely hemispherical, but can be comprised of a spherical section larger or smaller than a semi-(half) sphere. The cutter can be comprised of a spherical section greater than a hemisphere if a deeper, larger sample is desired. The cutter can also be comprised of a spherical section of less than hemispherical dimensions if a smaller, shallower sample is desired.

One significant beneficial result of the subject invention is the nature of the sample obtained for analysis As can be seen in FIGS. 13C-E, once sample 110 has been cut and retrieved, it can be accurately analyzed, because the original surface 88' of the sample remains undisturbed on the sample's upper surface. Another beneficial result of the subject invention is the nature of the remaining substrate after the sample is cut from it. As can be seen, the removal of sample 110 leaves a rather small dimple 109 with a fine surface finish in the surface of the sampled substrate which causes minimal disruption and structural weakening of it. By minimizing the kerf left by the blade portion 48 of cutter 25, through utilization of a thin blade, the disruption of material 80 is further minimized. Because cutter 25 is hemispherical in design blade portion 48 can be constructed extremely thin while still providing a very rigid blade. In many embodiments, a kerf of between 0.020" and 0.025" may be achieved by using a blade of 0.010" thickness and fine layer of grit of about 0.005" in thickness on each side while the structural rigidity necessary to maintain an accurate sampling of steel is still maintained.

Once given the above disclosure many other features, modifications and improvements will become apparent to the skilled artisan. Such features, modifications and improvements are thus to be considered a part of this invention, the scope of which is to be determined by the following claims:

I claim:

1. A method of cutting from a workpiece to be sampled a relatively small, preselected portion of the surface or surface and substrate of said workpiece and for retrieving said preselected portion for analysis apart from said workpiece without creating any substantial increase in stress in said workpiece whereby insufficient damage is caused to said workpiece to be detrimental to its continued use, the steps comprising:

locating a cutting means adjacent said preselected portion of the surface or surface and substrate of said workpiece to be sampled, driving said cutting means so as to enable it to cut said workpiece when brought into contact therewith, articulating said cutting means into contact with said workpiece, cutting said relatively small, preselected portion of the surface or surface and substrate from said workpiece by driving said cutting means while articulating said cutting means through a single arcuate path, thereby creating a relatively shallow, smooth depression in said workpiece, and retrieving said preselected portion for analysis after said cutting means separates said preselected portion from said workpiece.

2. A method according to claim 1 wherein said step of retrieving the preselected portion includes retaining said preselected portion within said cutting means.

3. A method according to claim 2 wherein said cutting means includes a semi-spherical blade means and said cutting step includes articulating said blade means, while rotating said blade means at cutting speed through said arcuate path from a first entrance location on a surface of said workpiece to a second exit location on a surface of said workpiece thereby to form a relatively shallow, non-destructive partial-spherical recess in the surface of said workpiece.

4. A method according to claim 3 wherein said step of retrieving the preselected portion further includes grinding the forwardmost edge of said portion as it is retained in said cutting means, thereby to accommodate it within said semispherical blade means for retrieval when said cutting step is completed.

5. A method according to claim 3 wherein said grinding is accomplished by a grinding ring disposed on an internal surface of said semi-spherical blade means.

6. A method according to claim 1 or 3 wherein said step of retrieving said preselected portion for analysis includes the step of attaching said portion to said cutting means by a magnet.

7. A method of sampling a workpiece by cutting from said workpiece to be sampled a relatively small, preselected portion of the surface or surface and substrate of said workpiece and for retrieving said preselected portion for analysis apart from said workpiece whereby insufficient damage is caused to said workpiece to be detrimental to its continued use, the steps comprising:

a cutting means comprised of locating a semi-spherical blade means in proximal cutting relationship to said preselected portion of said workpiece to be sampled, said blade means having an axis of rotation generally concentric with the center of said blade means and an axis of articulation substantially perpendicular to said axis of rotation, rotating said blade means about said axis of rotation at a speed capable of cutting said workpiece, articulating said blade means about said axis of articulation and into cutting engagement with said preselected portion of said workpiece, cutting said relatively small, preselected portion of the surface or surface and substrate from said workpiece by rotating said blade means about said axis of rotation at said cutting speed while articulating said blade means about said axis of articulation through an arcuate path until said preselected portion is separated from said workpiece, and retrieving said separated preselected portion by steps which include capturing and retaining said preselected portion within the interior portion of said semi-spherical blade means.

8. A method according to claim 7 wherein the step of retaining said preselected portion within the interior portion of said semi-spherical blade means includes the step of magnetically securing said portion to said interior portion of said blade means.

9. A method according to claim 7 wherein said cutting step includes articulating said blade means through said arcuate path from a first entrance location on a surface of said workpiece to a second exit location on a surface of said workpiece thereby to form a relatively shallow, non-destructive, partial-spherical recess in the surface of said workpiece.

10. A method according to claims 1, 7 or 9 wherein said cutting means is retained in a housing provided with means for locating said cutting means in proximal cutting relationship with said preselected portion, and which includes the further step of securing said cutting means to said workpiece once said cutting means is located in said cutting relationship with said preselected portion.

11. A method according to claim 10 wherein said housing includes a suspension means for carrying and positioning said cutting means, said suspension means normally biasing the housing and cutting means away from the preselected portion of said workpiece and raising said cutting means out of engagement with said preselected portion a sufficient distance to allow retrieval of said housing and cutting means after said preselected portion is cut from said workpiece, said housing further including means for overcoming the normal bias of said suspension means which when actuated lowers said cutting means into cutting relationship with said surface against said normal bias of said suspension means and wherein, said step of securing said cutting means to said workpiece once said cutting means is located in said cutting relationship with said preselected portion includes engaging a first portion of a surface of said workpiece with said suspension means and thereafter expanding said means for overcoming said normal bias into engagement with a second portion of a surface of said workpiece.

12. A method according to claim 11 wherein said expansion of said means for overcoming the normal bias of said suspension means, oversomes and acts against the normal bias of said suspension means and lowers said cutting means into proximal relationship with said preselected portion of said workpiece, thereby securing said cutting means in cutting relationship with said preselected portion by a combination of the normal bias of said suspension acting against the expanded means for overcoming said normal bias.

13. A method according to claim 12 wherein said means for overcoming the normal bias of said suspension means includes a fluid actuated cylinder means, and said step of expansion includes actuating said fluid actuated cylinder means.

14. A method according to claim 13 which further includes adjusting the cutting means prior to cutting, thereby to adjust the depth of the cut.

15. A method according to claim 14 wherein said preselected portion of a workpiece is an internal surface of a turbine-generator system.

16. A method of taking a metallurgical sample from a remote, internal surface of a generally inaccessible area within a turbine-generator without disassembling said generator so as to completely expose the area to be sampled, the steps including:

providing a probe of sufficiently small size to be moved through an orifice in said generator to a location for sampling, said probe comprising a housing having there within a cutting means, moving said probe through said orifice and adjacent the portion of surface to be sampled, such that said cutting means are in proximal relationship to said portion, securing said probe at said location, driving said cutting means so as to enable it to cut said portion when brought into contact therewith, articulating said cutting means into contact with said portion, cutting from said surface of said turbine-generator a relatively small, non-destructive sample by articulating said driven cutting means through a single arcuate path, thereby creating a relatively shallow, smooth depression in said surface, and retrieving said sample for analysis after said cutting means separates said sample from said surface.

17. A method according to claim 16 wherein said cutting means comprises a semi-spherical blade means having an axis of rotation generally concentric with the center of said blade means and an axis of articulation substantially perpendicular to said axis of rotation, said driving step comprising rotating said blade means about said axis of rotation at a speed capable of cutting said surface, and said articulation and cutting steps include articulating said blade means through a single arcuate path from one point on the surface to another, thereby to collect said sample within the interior portion of said blade means and create in said surface a non-destructive, relatively shallow, smooth partial-spherical recess, and retrieving said sample by moving said probe containing said sample within the interior of said blade means from the location of sampling to a point out of said orifice.

* * * * *